United States Patent [19]
LaGrone

[11] Patent Number: 5,981,493
[45] Date of Patent: Nov. 9, 1999

[54] METHOD OF TREATING HUMANS INFECTED WITH HUMAN IMMUNODEFICIENCY VIRUS

[76] Inventor: Robert P. LaGrone, 5408 McGavock Rd., Brentwood, Tenn. 37027

[21] Appl. No.: 08/274,201

[22] Filed: Jul. 13, 1994

Related U.S. Application Data

[63] Continuation of application No. 07/972,170, Nov. 5, 1992, abandoned.

[51] Int. Cl.$^6$ .......................... A61K 38/00; A61K 38/16
[52] U.S. Cl. .................................... 514/21; 514/2; 514/8; 514/12; 514/49; 514/50; 530/396; 424/85.7
[58] Field of Search .............................. 514/21, 2, 8, 12, 514/49, 50; 530/396; 424/85.91

[56] References Cited

U.S. PATENT DOCUMENTS

| | | | |
|---|---|---|---|
| 4,795,739 | 1/1989 | Lifson et al. | 514/8 |
| 4,869,903 | 9/1989 | Lifson et al. | 424/195.1 |
| 5,141,923 | 8/1992 | Byers et al. | 514/12 |

FOREIGN PATENT DOCUMENTS

WO91/04050  4/1991  WIPO .

OTHER PUBLICATIONS

Barbieri et al., "Volkensin, the Toxin of *Adenia Volkensii* (Kilyambiti Plant)", *FEBS Letters* 171(2):277–279 (1984).
Fernandez–Puentes et al., "Viral Infection Permeablizes Mammalian Cells to Protein Toxins", *Cell* 20:769–775 (1980).
Fodstad et al., "Phase I Study of the Plant Protein Ricin", *Cancer Res.* 44:862–865 (1984).
McGrath, et al., "GLQ223: An Inhibitor of Human Immunodeficiency Virus Replication in Acutely and Chronically Infected Cells of Lymphocyte and Mononuclear Phagocyte Lineage", *Proc. Natl. Acad. Sci. USA* 86:28445–28448 (1989).
Metzler et al., "Macrophages and the Human Immunodeficiency Virus", *Immunology Today* 11(6):217–223 (1990).
Olsenes et al., "Isolation and Properties of Abrin: A Toxic Protein Inhibiting Protein Synthesis", *Eur. J. Biochem.* 35:179–185 (1973).
Olsenes et al., "Purification and Characterization of the Highly Toxic Lectin Modeccin", *J. Biol. Chem.* 253(14):5069–5073 (1978).
Pauza, C.D., "HIV Persistence in Monocytes Leads to Pathogenesis and AIDS", *Cellular Immunol.* 112:414–424 (1988).
Simmons et al., "A Single Affinity Column Step Method for the Purification of Ricin Toxin from Castor Beans (*Ricinus communis*)", *Analytical Biochemistry* 146:206–210 (1985).
Simmons et al., "Mannose Receptor–Mediated Uptake of Ricin Toxin and Ricin A Chain by Macrophages", *J. Biol. Chem.* 261(17):7912–7920 (1986).
Till et al., "Human Immunodeficiency Virus–Infected T Cells and Monocytes are Killed by Monoclonal Human Anti–gp41 Antibodies Couples to Ricin A Chain", *Proc. Natl. Sci. USA* 86:1987–1991 (1989).
Yarchoan et al., "Anti–Retroviral Therapy of Human Immunodeficiency Virus Infection: Current Strategies of Challenges for the Future", *Blood* 78(4):859–884 (1991).
Zenilman et al., "Use of Ricin A–Chain to Selectively Deplete Kupffer Cells", *Journal of Surgical Research* 45:82–89 (1988).
Zenilman et al., "Selective Depletion of Kupffer Cells in Mice by Intact Ricin", *Transplantation* 41(1):200–203 (1989).
Ziska et al., "The Lectin from *Viscum Album* L. Purification by Biospecific Affinity Chromatography", *Experientia* 34:123–124 (1978).
Sandstrom et al, *Review Articles in Drugs*, vol. 34, No. 3, pp. 373–390, Sep. 1987.
Haynes, *Science*, vol. 260, pp. 1279–1286, May 28, 1993.
Fox, *Bio/Technology*, vol. 12, p. 128, Feb. 12, 1994.
Brown, *The Washington Post*, Jun. 10, 1993.
Greene, *Scientific America*, pp. 99–105, Sep. 1993 issue.
Fodstad et al, *Cancer Res.* vol. 44, pp. 862–865, 1984.
Yarchoan et al, *Blood*, vol. 78, No. 4, pp. 859–884, 1991.
Fernandez–Puentes et al, *Cell*, vol. 20, pp. 277–279, 1980.
Chaundhary et al, *Nature*, vol. 335, pp. 369–372, Sep. 22, 1988.

*Primary Examiner*—Robert J. Hill, Jr.
*Assistant Examiner*—Abdel A. Mohamed
*Attorney, Agent, or Firm*—Woodcock Washburn Kurtz Mackiewicz & Norris LLP

[57] ABSTRACT

A method of treating an individual who is suffering from human immunodeficiency virus infection is disclosed. The method comprises administering to a human who is suffering from human immunodeficiency virus infection, an amount of ricin, abrin, modeccin, viscumin or volkensin effective to eliminate mononuclear phagocyte

METHOD OF TREATING HUMANS INFECTED WITH HUMAN IMMUNODEFICIENCY VIRUS

CROSS REFERENCE TO RELATED PATENT APPLICATIONS

This application is a continuation of U.S. patent application Ser. No. 07/972,170 filed Nov. 5, 1992, now abandoned.

FIELD OF THE INVENTION

The present invention relates to a method of treating a human suffering from human immunodeficiency virus (HIV) infection by eliminating cells of mononuclear phagocyte lineage (MPL cells). More specifically, the present invention relates to a method of treating a human suffering from HIV infection by administering effective amounts of compounds such as double-chain ribosomal inactivating proteins (DC-RIPs) which eliminate MPL cells.

BACKGROUND OF THE INVENTION

Human immunodeficiency virus (HIV) is the etiological agent for acquired immune deficiency syndrome (AIDS). HIV infects cells of the immune system. In the course of the disease, the number of lymphocytes in the immune system becomes depleted, and the body is incapable of mounting a defense against other infections. Death eventually results as the immune system of an infected person becomes decreasingly effective in protecting the infected person.

HIV infects T-cells through CD4, a protein found on the cell membrane of those cells. The HIV protein gp120 binds to CD4 as the initial step in the infection of a T-cell by HIV. Upon infection, the virus replicates within the T-cell and eventually destroys the cell, yielding multiple virus particles which can then infect other T-cells. Thus, T-cells, cells which are part of the system that protects against infections, are the target of the infectious agent. At first, the immune system provides protection and disease development from initial HIV infection to AIDS is slow. As the infection progresses, the immune system become increasingly depleted and compromised. Finally, the immune system becomes incapable of adequately functioning and death results, usually by an opportunistic infection the body is incapable of defending against.

There is no cure for AIDS and the treatments currently available are ineffective at substantially lengthening life. Moreover, the therapy available to prevent people infected with HIV from developing AIDS is equally ineffective. Given the exponential growth of this pandemic, it is estimated that up to 40 million people will be infected with HIV by the year 2000. A treatment must be found that is capable of extremely large, rapid, inexpensive production or possibly every one of the estimated 40 million people will die prematurely. There is a critical need for a more effective treatment for people suffering from AIDS. Furthermore, there is a need for a more effective therapy for people who are HIV positive but do not have AIDS in order to prevent them from developing AIDS.

Both the government and the pharmaceutical industry have devoted vast resources to finding an effective treatment for people infected with HIV. The commitment of money and man-power has been significant in an effort to overcome this currently intractable problem which defies a solution. Enormous amounts of money have been earmarked and spent on research. Large numbers of scientists are actively engaged in AIDS research, and in particular, in drug discovery efforts to identify compounds and methods to stop or slow the destructive progress of the virus in infected people.

Currently, a great deal of effort is being made to discover compounds and methods that prevent or retard HIV replication and the destruction of the immune system in infected persons. Although some progress has been made, there have been no discoveries that vastly increase the life expectancy of infected persons.

One strategy is to interfere with viral enzymes essential for viral replication. There is a great deal of interest in finding compounds that inhibit HIV reverse transcriptase (RT) or HIV protease. Currently, some success has been made using RT inhibitors. However, it has been only limited success. Over time, RT inhibitors appear to lose their effectiveness.

Another approach to combatting the virus is to selectively destroy infected T-cells by targeting gp120 using CD4 conjugated to a toxin or antigen. The CD4-conjugate is supposed to bind to gp120 associated with infected cells. In the case of CD4-toxin conjugates, the toxin is then available to kill the cell and thereby prevent viral replication. If a CD4-antigen conjugate is used, the CD4-conjugate that is bound to the infected cell will provide a good target for removal by the immune system before viral replication is complete. The infected cell will be killed and its contents destroyed. Thus far, no successful treatment has been developed from these efforts.

Many other strategies and approaches have also been employed. However, despite the desperate need and the enormous drug discovery effort, no successful treatment has been developed to stop or effectively slow the progress of infection from initial viral infection to the eventual destruction of the immune system characteristic of AIDS.

C. D. Pauza, (1988) Cellular Immunol. 112:414–424, reports that infected monocytes act as reservoirs of HIV, and further are involved in presentation of HIV to T-cells. Pauza discusses the need to focus more attention on the effects that the progression of AIDS has on monocyte cells and the breakdown of natural immunity associated with HIV infection of them. Pauza relates that the abrogation of normal effectiveness of monocyte cells in natural immunity caused by HIV infection of monocytes results in the sensitivity an individual has to opportunistic infections. Rather than targeting monocyte cells, however, Pauza discusses the deleterious effects on the HIV-infected individual caused by the lack of functional monocytes. The link is drawn between the lack of normally functioning monocytes and fatality in HIV infected individuals.

Metzler, et al., (1990) Immunology Today 11(6):217–223 review the role of macrophage cells in HIV disease. A discussion of persistently infected cells in the pathological development of HIV infection is included. Metzler et al. disclose the need to control HIV infection and replication in macrophages, and neither teach nor suggest the elimination of the cells.

McGrath, M. S. et al., (April 1989) Proc. Natl. Acad. Sci. USA 86:2844–2848, describe a compound, GLQ223, which is reported to inhibit HIV replication in vitro in cultured lymphocytes and mononuclear phagocytes. GLQ223, a 26kD protein that is purified from plant material, is similar in function and structure to the A chain of Ricin. McGrath et al. acknowledged the need for targeting HIV in mononuclear phagocytes as necessary for effectively impeding the advancement of disease. However, GLQ223 is directed at eliminating viral replication in monocytes, not elimination of monocytes themselves.

U.S. Pat. No. 4,869,903 issued Sep. 26, 1989 to Lifson et al. relates to a method of selectively inhibiting HIV in T-lymphocytes and monocytes that have been infected with HIV. The method comprises exposing infected cells to a plant derived single chain ribosome inactivating protein and inhibiting HIV replication while not destroying infected cells.

U.S. Pat. No. 4,795,739 issued Jan. 3, 1989 to Lifson et al. relates to a method of inhibiting expression of HIV antigens in T-lymphocytes and monocyte/macrophage cells that are infected with HIV. A method of treating human subjects infected with HIV is also disclosed. The specification contains a discussion of the problem caused by persistently infected monocyte/macrophage cells in the development of the disease in infected individuals. Two compounds, trichosanthin (TCS) and momorcharin (MMC), both of which are plant derived proteins, are disclosed as effective agents to inhibit expression of viral antigens in monocytes/macrophage cells that are infected with HIV. To solve the problem posed by persistently infected monocytes/macrophage cell, TCS and MMC are used to inhibit viral replication and production of viral proteins. There is no suggestion of destroying monocytes/macrophage cells. The disclosure contains instructions on screening compounds for anti-HIV activity. The screening assays are directed at identifying compounds which inhibit expression of viral antigens HIV infected monocytes/macrophage cells. Ricin, Abrin and Modeccin are among the compounds which are suggested to be used in the screening assay used to determine whether or not compounds inhibit expression of viral antigens in monocytes/macrophage cells. Both intact and A-chain forms of these compounds are suggested for screening. The method disclosed is directed at inhibiting viral replication and production of viral proteins without loss of viability to infected cells. The aim of the invention is to inhibit viral replication while not harming the cells.

Ricin, also know as Ricin D and RCA-II, is a monovalent lectin derived from caster beans. Ricin, a toxin, is composed of two dissimilar peptide chains. The B-chain is responsible for binding to, and facilitating entrance into, the target cell. Upon entering the cell, the A-chain enzymatically inactivates the 60S ribosomal subunit, thereby inhibiting protein synthesis and causing cell death by apoptosis.

Simmons, B. M. et al., (1986) J. Biol. Chem. 261(17):7912–7920, disclose the role of the high mannose carbohydrate chains in the mechanism of action of Ricin toxin. The mannose receptor-mediated uptake of Ricin toxin and Ricin A chain by macrophages is discussed as well as the binding of the Ricin galactose receptor to cell surface glycoproteins. The role of carbohydrate in the multiple intracellular pathways for chain translocation were investigated.

Zenilman, M. E. et al., (1989) Transplantation 47(1):200–203, reports that intraportal administration of intact Ricin to mice resulted in the selective depletion of Kupffer cells. Zenilman et al. suggest that selective depletion of donor Kupffer cells prior to organ transplantation may decrease donor immunogenicity and therefore reduce rejection. Zenilman et al. report that intact Ricin is significantly more effective than Ricin A-chain alone in depletion of Kupffer cells.

For the past decade, immunotoxins have been formed using either Ricin A-chain or intact Ricin conjugated with a specific targeting antibody. The antibody is directed at a cell surface protein or a viral protein that is displayed on the surface of virally infected cells. When a cell ingests the Ricin-antibody complex bound to its surface, the cell is killed. Great efforts have been made to try and bypass the "natural tendency" for these immunotoxins to be removed from the bloodstream by macrophages in the spleen and liver. The greatest success at reducing this undesired macrophage toxicity has been through the elimination of Ricin's carbohydrate side chain.

In addition to Ricin, other ribosome-inactivating proteins include Abrin, Modeccin, Viscumin and Volkensin.

Abrin, another monovalent lectin, is a protein extracted from *Abrus precatorius* seeds. Abrin, similar to Ricin, is a toxin comprised of dissimilar peptide chains.

Modeccin, another toxic lectin, is also a ribosomal-inactivating protein derived from plants. Modeccin can be extracted from the root of *Adenia digitata*. Modeccin is also composed of two dissimilar peptide chains.

Viscumin is a toxic lectin that very similar to Ricin. Viscumin, which is also comprised of two dissimilar peptide chains, is extracted from *Viscum album* L. (mistletoe)

Volkensin, another toxic lectin, is also a ribosomal inactivating protein derived from plants. Volkensin can be extracted from *Adenia volkensii*. Volkensin is also composed of two dissimilar peptide chains.

The present invention provides a method of treating humans suffering from HIV infection by administering compounds which selectively eliminate MPL cells. According to the invention, MPL cells are selectively targeted for destruction in order to eliminate them as HIV reservoirs. By selectively destroying MPL cells, the advancement of HIV infection is disrupted by interfering with a mechanism of HIV proliferation in which the virus is maintained in the body and presented to T-cells, furthering the replication of the virus. According to the invention, HIV can be eradicated or the progress of the infection severely curtailed in an individual by eliminating the reservoir which enables HIV to persist during the body's effort to remove it.

SUMMARY OF THE INVENTION

The present invention relates to a method of treating a human that is infected with HIV by selectively eliminating mononuclear phagocyte lineage cells.

DETAILED DESCRIPTION OF THE INVENTION

As used herein, the term "toxic lectins", "ribosomal inactivating proteins" (RIP), "RIPs", "double-chain ribosomal inactivating proteins" (DC-RIPs), and "DC-RIPs" are interchangeable and refer to Ricin, Abrin, Modeccin, Viscumin and Volkensin.

As used herein, "MPL cells" refers to cells of mononuclear phagocyte lineage. "Cells of the Mononuclear Phagocyte lineage" are called monocytes within blood vessels and become macrophages, Langerhan's cells, or Kupffer cells, depending on which tissue of the body is entered. Langerhan's cells, and possibly others, then occasionally migrate to the spleen to become Dendritic cells.

MPL cells are persistently infected with HIV and play a critical role in the development of AIDS. When HIV infects these cells, abundant virus is produced. It is estimated infected MPL cells produce 10 times more viral particles per cell than infected T-cells; furthermore, cells of the mononuclear phagocyte lineage are resistant to the cytopathic effects of the infection, and chronic infection is established. Because they do not display surface viral proteins to the extent virally infected T-cells normally do, infected MPL cells harboring HIV are not identified and extricated by the immune system.

Interactions between infected MPL cells and T-cells results in virus dissemination. Fulfilling their normal role as antigen presenting cells, the macrophage present HIV to the T-cells. As the slowly increasing number of infected MPL cells continue to present HIV to helper T-cells, the helper T-cell population becomes infected in increasing numbers. As the result of this viral infection of T-cells and the subsequent viral replication therein, the number of helper T-cells decreases, thereby reducing the immune systems capacity to function. A weakened immune system allows for increased numbers of infected MPL cells which continue to present HIV to T-cells resulting in destruction of more T-cells. The immune system becomes more weakened as more T-cells are destroyed by HIV infection and more virus is produced. Eventually, the immune system is so compromised that the patient is susceptible to opportunistic infections which the patient cannot defend against. The patient dies from such infections.

The establishment of chronic infection of MPL cells renders therapies based solely upon inhibition of HIV in T-cells insufficient to fully combat HIV and delay the onset of AIDS for any appreciable time. MPL cells are reservoirs for HIV and it is suspected that infection of circulating CD4(+) T-cells is rare, occurring in only 1 of 12,000 cells. Targeting infected T-cells will not eradicate the virus. In the later stages of differentiation, MPL cells lose their CD4 (+) marking, making "anti-CD4 therapy" ineffective against the true viral reservoir. Further, once the retrovirus has become a "pro-virus", reverse transcriptase becomes unnecessary and the currently available inhibitors are also ineffective. As a result, every HIV infection remains lethal.

Bone marrow transplantation is likewise unable to prevent progressive HIV infection. Despite chemotherapy to completely eliminate the patient's bone marrow and circulating white blood cells followed by the reconstitution of a new immune system through the introduction of a donor's marrow, the virus still escapes destruction. The ablative chemotherapy does not eliminate tissue macrophages. Thus, despite some success in developing effective treatments, persistently infected MPL cells will remain and allow for the continued presence of the virus.

Although it is known that MPL cells represent a virus reservoir which provide for the chronic persistence of virus, there has been no teaching or suggestion of eliminating these cells. The focus of the problem posed by MPL cell virus reservoirs has been the effects that the progression of AIDS has on MPL cells in connection with the breakdown of natural immunity associated with HIV infection of MPL cells. Thus, it has been suggested that there is a need to address the abrogation of the normal effectiveness of MPL cells in natural immunity which results in the sensitivity an individual has to opportunistic infections. Rather than targeting MPL cells, the focus of attention has been to try to counteract the deleterious effects that the lack of functional MPL cells has on the HIV-infected individual caused. Moreover, another area of research has focussed on the need to control HIV infection and replication in macrophage cells but not the elimination of the cells themselves. A great deal of effort has been directed at the need for compounds which effectively prevent viral gene expression and viral replication while not being toxic to the cells. There exist no teachings or suggestions to target the virus reservoir for elimination. There are no drugs currently available which are designed to selectively eliminate MPL cells.

The present anti-HIV therapies and strategies do not address critical mechanisms in the pathology of HIV infection. A more demanding and fundamental attack on the virus is necessary in order to effectively treat and/or cure a patient. In order to effectively combat HIV, important cells of the immune system must be eliminated i.e., destroyed. The viral reservoir must be removed in order to effectively oppose HIV dissemination and AIDS development. All efforts to eliminate the virus by natural means or otherwise are undermined by the persistent HIV infection of MPL cells. Accordingly, the MPL cells must be a target for elimination.

The invention relates to a method of treating HIV-infected humans by selectively eliminating the MPL cells. The invention also relates to a method of preventing or slowing depletion of T cells in a human suffering from human immunodeficiency virus infection by selectively eliminating the MPL cells. These virus reservoir cells play an essential role in the pathology of HIV and by specifically attacking them, it is possible to slow the progress of the infection and, especially when done in conjunction with other therapies, arrested the disease.

According to the invention, there are many different ways to delete MPL cells. Such methods include administration of double-chain ribosomal inactivating proteins such as Ricin, Abrin, Modeccin, Viscumin, and Volkensin. In addition, MPL cells may be eliminated by other means including, but not limited to, administration of silica or toxins enveloped within liposomes or by infusing long-acting adenosine analogs. DC-RIPs provide the most effective means to selectively eliminate the mononuclear phagocyte lineage reservoir. The double-chain ribosomal inactivating proteins such as Ricin, Abrin, Modeccin, Viscumin, and Volkensin are particularly useful as anti-HIV compounds because of their specific properties which render MPL cells more susceptible than other cell types to the toxic effects associated with these lectins.

MPL cells including Kupffer cells, Langerhans cells and pulmonary macrophages, are more sensitive to the effects of toxic lectins such as intact Ricin, presumably due to increased uptake through mannose receptors on these cells. However, Fc-receptor uptake and non-specific phagocytosis-pinocytosis also seem to be involved. Further, protein synthesis in MPL cells seems unusually sensitive to the effects of toxins such as Ricin.

DC-RIP's are capable not only of providing mannose and galactose side-chains for MPL cells to bind, but also of binding certain other carbohydrates themselves. Because gp120, the HIV surface protein on infected T-cells, contains a number of these same carbohydrate moieties, it is probable the DC-RIP's have an independent affinity for infected T-cells beyond their effect on MPL cells. Internalized DC-RIP would cause T-cell death by apoptosis, as well as the abrupt termination of actively replicating virus. Patient blood samples may be cell sorted using fluorescent-labeled anti-gp120 antibody to demonstrate reduction with treatment, thereby indicating whether this additional effect actually takes place in infected humans.

MPL-selective toxins generally, and DC-RIPs in particular, can be used as effective anti-retroviral agents because when administered to infected persons at a proper dosage, these agents are selectively taken up by MPL cells which are thereby killed without causing toxic side effects to the patient. Intact double-chain ribosomal inactivating proteins such as Ricin, Abrin, Modeccin, Viscumin and Volkensin can be administered to a human infected with HIV to eliminate MPL cells and thereby reduce the availability of these cells to become persistently infected viral reservoirs.

Effective dosages of intact Ricin, Abrin, Modeccin, Viscumin and Volkensin sufficient to selectively eliminate MPL cells do so without side effects. Toxic lectins selectively bind to and are taken up by cells by a variety of mechanisms.

The HIV infected MPL cell reservoir that is exposed to Ricin, Abrin, Modeccin, Viscumin and Volkensin is removed through non-specific phagocytosis, mannose and galactose receptor-mediated phagocytosis, and Fc-receptor mediated phagocytosis. Moreover, there is an unusual sensitivity of protein synthesis in MPL cells for Ricin, Abrin, Modeccin, Viscumin and Volkensin. Accordingly, although these toxic lectins are highly toxic to all cells, MPL cells have a greater tendency to take in these lectins and, therefore, can be eliminated selectively by low doses of Ricin, Abrin; Modeccin, Viscumin and Volkensin which are otherwise non-toxic.

MPL cell elimination occurs through apoptosis; thus, virus particles are not allowed to escape the dying cell. Ingestion of the dying MPL cell by macrophages allows for virus to be killed in the lysosomes of the latter.

In cases of Fc-mediated phagocytosis, the developing antibody response of the patient against this foreign protein will not significantly reduce effectiveness. Antibody/toxin complexes can effectively eliminate MPL cells. This "acquired resistance" has been a major disadvantage of immunotoxins because the targeting antibody is neutralized and macrophages clear the complex.

Double-chain ribosomal inactivating proteins selectively eliminate MPL cells. For example, the MPL cells of the liver, Kuppfer cells, are 100 to 1000 times more sensitive to double-chain ribosomal inactivating proteins such as Ricin than are other cells such as hepatocytes. As discussed above, Zenilman (1989) has shown that a double-chain ribosomal inactivating protein, Ricin, injected intraperitoneally is capable of eliminating 45% of Kupffer cells without any morbidity. It is worth noting that the dose given in that experiment of 1.0 micrograms/kg is below the LD-50, that is, the dose at which 50% are expected to die, of 2.7 micrograms/kg. Single-chain RIPs such as Ricin A-chain require 20,000 times higher doses (20 mg/kg given over 4 days) to achieve Kupffer cell elimination rates of 27% (See Zenilman et al., (1988) J. Surg. Res. 45:82–89).

Human studies have been performed to document the safety of Ricin. Fodstad, O. et al, (1984) Cancer Res. 44:862–865 which is incorporated herein by reference, disclose Phase I clinical studies using intact Ricin with cancer patients to determine the maximum tolerated doses. It is reported that doses up to 20 micrograms/square meter body surface are well below toxic levels.

HIV-infected MPL cells are more sensitive to the toxins than non-infected MPL cells. In general, viruses make cells 50–500 times more sensitive to toxins. Fernandez-Puentes, C. and L. Carrasco, (1980) Cell 20:769–775 disclose that viral infection increases cell membrane permeability. It is disclosed in U.S. Pat. No. 4,869,903, described above, that single-chain ribosomal inactivating proteins are 50–60 times more toxic in HIV infected lymphocytes compared to uninfected control lymphocytes.

Cellular protein synthesis in non-virally infected cells is inhibited by double-chain ribosomal inactivating proteins in concentrations of 3–10 nanograms/ml. With toxin efficacy increasing up to 500-fold during viral infection, double-chain RIP's kill cells in HIV(+) people at picogram/ml quantities.

Non-toxic, selective MPL cell elimination is possible at "reasonable" doses. The increased sensitivity of virally-infected cells dramatically improves the risk:benefit ratio, given the very steep dose-response curve for DC-RIP's.

MPL cell elimination from the body is transient; less than 20% of MPL cells can be eliminated by any single dose of a DC-RIP without causing non-specific damage. Therefore, the normal function of MPL cells in the body (red cell clearance, tumor surveillance, etc.) is not severely impaired. Unlike other lectins, Abrin and Ricin are not toxic to the central nervous system. Further, Abrin is not toxic to peripheral nerves, even when injected into them. Moreover, there is no bone marrow toxicity associated with the administration of intact Ricin or Abrin.

A typical treatment regimen will consist of administration at the highest dose possible, between about 1 and about 20 micrograms, depending on which of the five DC-RIP's is being used, without causing any undesired side effect, such as nausea, myalgia, or increased hepatic enzymes (SGOT, SGPT, Alkaline phosphatase, bilirubin). Treatment continues on a regular basis every 2–4 weeks until plasma HIV p24 antigen is no longer detected. Thereafter, the same double-chain ribosomal inactivating protein may be reinstituted, should p24 antigen reappear in the serum.

The development of atopic reaction or a substantial, specific IgE or IgG level against a given double-chain RIP, warrant switching to a second, immunogenically non-cross reactive double-chain RIP. It is known Ricin, Abrin and Modecccin are all immunogenically non-cross reactive. The development of small quantities of specific IgG should not interfere greatly with toxicity toward MPL cells, as Fc-receptor mediated phagocytosis should replace that mediated by carbohydrate; however, eventually the non-specific uptake by other cell lines possessing Fc receptors may lead to undesired toxicity (anemia, neutropenia, hematuria, etc.), and administrating a different DC-RIP is indicated.

The present invention provides a new weapon in the arsenal to treat HIV infection and can be used in concert with other therapies. Intact Ricin, Abrin, Modeccin, Viscumin or Volkensin can be used together with other anti-retroviral drugs, especially reverse transcriptase inhibitors such as Zidovudine or other available inhibitors of reverse transcriptase in standard doses. In general, the DC-RIP's can be used with any other anti-retroviral therapy. By practicing the present invention as a co-therapy with other treatments and medications, more than one mechanism by which the virus perpetuates itself in the patient can be targeted. Combatting the virus at multiple points of its infectious cycle hinders the progress of disease and the onset of AIDS is prevented or delayed.

Toxic lectins which can be used in the method of the present invention include Ricin, Abrin, Modeccin, Viscumin and Volkensin. A preferred toxic lectin used in the method of the present invention is Ricin.

A preferred embodiment of the present invention is a method of treating a human suffering from HIV which comprises administering an effective amount of Ricin. A preferred dosage range is between about 0.0001 and about 30 micrograms. A more preferred dosage range is about 1 to about 20 micrograms.

Intact Ricin is very easy and inexpensive to produce. Large quantities can be produced by well know methods from readily available starting materials. Simmons B. M. and J. H. Russell, (1985) Analytical Biochemistry 146:206–210, which is incorporated herein by reference., describe a single affinity column step method for the purification of Ricin toxin from castor beans.

Abrin can be extracted from *Abrus precatorius* seeds. Olsnes, S. and A. Phil, (1973) Eur. J. Biochem. 35:179–185, incorporated herein by reference, disclose a method of extraction and purification of Abrin from semen jegwiriti.

Modeccin can be extracted from the root of *Adenia digitata*. Olsnes A. et al., (1978) J. Biol. Chem. 253(14):5069–5073, incorporated herein by reference, disclose a method of extraction and purification of- Modeccin from *Adenia digitata*.

Viscumin can be extracted from *Viscum album* L. (mistletoe). Ziska, P. et al., (1978) Experientia 34:123–124 incorporated herein by reference, disclose a method of extraction and purification of Viscumin from *Viscum album* L.

Volkensin can be extracted from Adenia volkensii. Barbieri, L. et al., (1984) FEBS 171(2):277-279 incorporated herein by reference, disclose a method of extraction and purification of Volkensin from *Adenia volkensii*.

Fodstad, O. et al., discussed above and incorporated herein by reference, disclose a phase I study of Ricin on cancer patients. The purification, formulation and administration of Ricin is described. Tolerated dose levels are disclosed.

To practice one embodiment of the invention, intact Ricin can be purified following the teachings of Simmons and Russell or Fodstad et al. Ricin can be formulated as described by Fostad et al. and administered to patients infected with HIV. Non-toxic doses effective for the selective eliminating macrophages can be determined by routine methods.

In addition to the destruction of MPL cells in order to eliminate them as viral reservoirs, the present invention provides further benefits. Virally infected MPL cells secrete cytokines and amplify T-cell:macrophage interaction, causing more rapid dissemination of the infection. Elimination of activated macrophages will reduce cytokine (Il-1, TNF, Il-6) levels, lower infected macrophage/T-cell interactions, and slow progression of the illness.

It is contemplated that according to another aspect of the invention, the selective elimination of MPL cells can be undertaken to reduce cytokine levels that occur during certain illnesses and disorders. Any disease characterized by high secretion of macrophage cytokines including Interleukin-1 or tumor necrosis factor, for example, can be treated by selective elimination of MPL cells, especially the administration of DC-RIPs. Such diseases include alcoholic cirrhosis, rheumatoid arthritis, systemic vasculitis or others. Furthermore, while there are no other known retroviral infections in humans besides HIV type 1 and 2, and Human T-cell Leukemia Virus (HTLV) other diseases such as, for example, systemic lupus erythematosus, Sjogrens syndrome or other collagen vascular disease may represent retroviral infections. If chronic retroviral infection of MPL cells plays a role in these disease, the invention can be used to selectively eliminate the MPL cells. There are certain parasitic infections, such as Leishmaniasis, which localize to MPL cells. Accordingly, such infections can be treated by selective elimination of MPL cells, especially by administration of DC-RIPs. Finally, MPL cells which are not killed by doses of chemotherapy and which are responsible for acute or chronic graft-versus-host disease during bone marrow or other organ transplantation, may be eliminated and will vastly increase the potential of this therapy.

EXAMPLE

Ricin is purified as described by Fodstad, O. et al. Assuming a 5 liter blood volume, only nanograms of protein are necessary to obtain elimination of MPL cells in HIV infected individuals. Given the maximal doses attainable in humans without any noticeable side effect is about 25–30 micrograms, the range of non-toxic therapeutic efficacy is between about 0.001 and about 30 micrograms.

Though capable of storage in 50% glycerol for 2 years, the protein is delivered parenterally in solution comprising 0.03% human serum albumin in normal saline with 10% glycerol as stabilizer, by subcutaneous, intramuscular or intravenous injection. Alternatively, it may achieve slower absorption by liposome-encapsulation, or enmeshed in a slow-releasing substance like collagen matrix. Though capable of attachment to other proteins, these toxins have unique value because of their "natural binding" and increased toxicity specifically to MPL cells.

To document the depletion of MPL cells, hepatic scans using technicium-99-labeled sulfur colloid may be used. Quantitively, Kupffer cells are the most numerous MPL cells in the body, and Kupffer cell reduction may be assessed by reduced uptake of the sulfur colloid in the liver. As this type of hepatic scan is routinely performed in nearly all hospitals, the determination of DC-RIP activity will be readily available to many research centers around the world. While it will not be necessary to quantitate MPL cell reduction in routine patients, colloidal scans will be helpful to maximize effect during early testing. When used, such scans are preferably performed 24–48 hours after infusion of the DC-RIP. Because of rapid non-infected cells replacement, even after extensive infected MPL cell elimination, MPL cell levels will return to normal in 7–10 days.

Adverse reactions occurring within twenty four hours of administration may be minimized by dexamethasone 8 mg given intravenously or orally every 6 hours. Dexamethasone upregulates mannose receptors and hastens serum clearance; this corticosteroid also minimizes cytokine production and stops allergic reactions by stabilizing mast cells. Infusions of lactose or mannan would similarly compete with the DC-RIP for the carbohydrate-biding sites on the MPL cells, and thereby minimize effect. If available for use in human, infusions of either lactose or mann are optional procedures to treat patients suffering adverse reactions.

I claim:

1. A method of treating a human suffering from human immunodeficiency virus infection comprising:

administering to said human parenterally by subcutaneous, intramuscular or intravenous injection of intact, unconjugated double chain ribosomal inactivating protein selected from the group consisting of: ricin, abrin, modeccin, viscumin and volkensin in an amount therapeutically effective in reducing the number of mononuclear phagocyte linage cells in said human.

2. The method of claim 1 wherein the amount of ricin, abrin,modeccin, viscumin or volkensin administered to said human is between about 0.0001 and about 30 micrograms.

3. The method of claim 1 wherein the amount of ricin, abrin, modeccin, viscumin or volkensin administered to said human is between about 1 and about 20 micrograms.

4. The method of claim 1 wherein said human is undergoing anti-retroviral therapy, wherein said anti-retroviral therapy comprises administration of an antiviral agent.

5. The method of claim 4 wherein said anti-viral agent is a human immunodeficiency virus reverse transcriptase inhibitor.

6. The method of claim 5 wherein said anti-viral agent is zidovudine.

7. The method of claim 6 wherein the amount of ricin, abrin, modeccin, viscumin or volkensin administered to said human is between about 0.0001 and about 30 micrograms.

8. The method of claim 7 wherein the amount of ricin, abrin, modeccin, viscumin or volkensin administered to said human is between about 1 and about 20 micrograms.

9. A method of preventing depletion of T cells in a human suffering from human immunodeficiency virus infection comprising:

administering to said human parenterally by subcutaneous, intramuscular or intravenous injection of intact, unconjugated double chain ribosomal inactivating protein ricin in an amount therapeutically effective in reducing the number of mononuclear phagocyte lineage cells in said human.

10. The method of claim 9 wherein the amount of ricin administered to said human is between about 0.0001 and about 30 micrograms.

11. The method of claim 9 wherein the amount of ricin administered to said human is between about 1 and about 20 micrograms.

12. The method of claim 9 wherein said human is undergoing anti-retroviral therapy, wherein said anti-retroviral therapy comprises administration of an antiviral agent.

13. The method of claim 12 wherein said anti-viral agent is a human immunodeficiency virus reverse transcriptase inhibitor.

14. The method of claim 13 wherein said anti-viral agent is zidovudine.

15. The method of claim 14 wherein the amount of ricin administered to said human is between about 0.0001 and about 30 micrograms.

16. The method of claim 14 wherein the amount of ricin administered to said human is between about 1 and about 20 micrograms.

17. A method of treating a human suffering from human immunodeficiency virus infection comprising:

administering to said human parenterally by injection of intact, unconjugated ricin in an amount therapeutically effective in reducing the number of mononuclear phagocyte lineage cells in said human including mononuclear phagocyte lineage cells harboring human immunodeficiency viral genomes;

wherein reduction of mononuclear phagocyte lineage cells in said human including reduction of mononuclear phagocyte lineage cells harboring human immunodeficiency viral genomes provides a therapeutic effect on said human suffering from human immunodeficiency virus infection.

18. A method of claim 17 wherein the amount of ricin administered to said human is between about 0.0001 and about 30 micrograms.

19. The method of claim 17 wherein said human is undergoing anti-retroviral therapy wherein said anti-retroviral therapy comprises administration of an antiviral agent.

20. The method of claim 19 wherein said anti-viral agent is a human immunodeficiency virus reverse transcriptase inhibitor.

* * * * *